US012592309B2

(12) United States Patent
Bondar et al.

(10) Patent No.: US 12,592,309 B2
(45) Date of Patent: Mar. 31, 2026

(54) AUTOMATED DETECTION OF LUNG CONDITIONS FOR MONITORING THORACIC PATIENTS UNDERGOING EXTERNAL BEAM RADIATION THERAPY

(71) Applicant: Elekta, Inc., Atlanta, GA (US)

(72) Inventors: Maria Luiza Bondar, Waalre (NL); Jacek Lukasz Kustra, Eindhoven (NL); Sergio Consoli, Nuenen (NL)

(73) Assignee: Elekta, Inc., Atlanta, GA (US)

(*) Notice: Subject to any disclaimer, the term of this patent is extended or adjusted under 35 U.S.C. 154(b) by 477 days.

(21) Appl. No.: 17/417,406

(22) PCT Filed: Dec. 16, 2019

(86) PCT No.: PCT/EP2019/085212
§ 371 (c)(1),
(2) Date: Jun. 23, 2021

(87) PCT Pub. No.: WO2020/136028
PCT Pub. Date: Jul. 2, 2020

(65) Prior Publication Data

US 2022/0076802 A1 Mar. 10, 2022

(30) Foreign Application Priority Data

Dec. 24, 2018 (EP) .................................... 18215837

(51) Int. Cl.
*G16H 20/40* (2018.01)
*A61N 5/10* (2006.01)
(Continued)

(52) U.S. Cl.
CPC ........... *G16H 20/40* (2018.01); *A61N 5/1039* (2013.01); *G06N 20/00* (2019.01); *G16H 10/60* (2018.01);
(Continued)

(58) Field of Classification Search
None
See application file for complete search history.

(56) References Cited

U.S. PATENT DOCUMENTS

| | | | |
|---|---|---|---|
| 9,122,959 | B2 | 9/2015 | Zhou |
| 10,022,560 | B2 | 7/2018 | Kumar |

(Continued)

FOREIGN PATENT DOCUMENTS

| | | |
|---|---|---|
| CN | 102822834 | 12/2012 |
| CN | 104703541 | 6/2015 |

(Continued)

OTHER PUBLICATIONS

Tvilum, Marie et al "Clinical outcome of image-guided adaptive radiotherapy in the treatment of lung cancer patients," Acta Oncol., vol. 54, No. 9, pp. 1430-1437, Oct. 2015.

(Continued)

*Primary Examiner* — Robert W Morgan
*Assistant Examiner* — Edward B Winston, III
(74) *Attorney, Agent, or Firm* — Schwegman Lundberg & Woessner, P.A.

(57) ABSTRACT

A computerized system (SRS) for radiation therapy support. The system comprises an input interface (IN) for receiving an input image acquired by an imaging apparatus (IA1). The input image represents a region of interest (ROI) internal of a patient (PAT) and acquired before delivery of a dose fraction by a radiation therapy delivery apparatus (RTD). A pre-trained machine learning unit (MLU) of the system is configured to process the input image to detect a medical condition. A communication component (RC) of the system is configured to provide, based on the detected medical condition, an indication for one or more clinical actions to be performed in relation to the patient.

19 Claims, 7 Drawing Sheets

(51) Int. Cl.

| | |
|---|---|
| ***G06N 20/00*** | (2019.01) |
| ***G16H 10/60*** | (2018.01) |
| ***G16H 30/20*** | (2018.01) |
| ***G16H 30/40*** | (2018.01) |
| ***G16H 40/20*** | (2018.01) |
| ***G16H 40/67*** | (2018.01) |
| ***G16H 50/20*** | (2018.01) |
| ***G16H 50/70*** | (2018.01) |

(52) U.S. Cl.

CPC ............. *G16H 30/40* (2018.01); *G16H 40/67* (2018.01); *G16H 50/20* (2018.01); *G16H 50/70* (2018.01); *A61N 2005/1074* (2013.01); *G16H 30/20* (2018.01); *G16H 40/20* (2018.01)

(56) References Cited

U.S. PATENT DOCUMENTS

| | | | | |
|---|---|---|---|---|
| 10,282,588 | B2 | 5/2019 | Comaniciu | |
| 10,350,438 | B2 | 7/2019 | Brooks | |
| 10,456,595 | B2 | 10/2019 | Ribbing | |
| 11,033,254 | B2 | 6/2021 | Hautvast | |
| 11,056,243 | B2 | 7/2021 | Sjolund | |
| 11,517,197 | B2 * | 12/2022 | Zhou | G06T 11/005 |
| 11,517,768 | B2 * | 12/2022 | Hibbard | A61N 5/1039 |
| 11,551,353 | B2 * | 1/2023 | Golden | G06N 3/09 |
| 2009/0234627 | A1 * | 9/2009 | Yu | A61N 5/1031 703/11 |
| 2015/0216489 | A1 | 8/2015 | Everaerts | |
| 2016/0140300 | A1 | 5/2016 | Purdie | |
| 2016/0321427 | A1 | 11/2016 | Bogoni | |
| 2018/0039726 | A1 | 2/2018 | Boissel | |
| 2018/0214105 | A1 | 8/2018 | Anavi | |
| 2018/0214714 | A1 | 8/2018 | Carpenter | |
| 2018/0294052 | A1 | 10/2018 | Fishman | |

FOREIGN PATENT DOCUMENTS

| | | | | |
|---|---|---|---|---|
| CN | 105407966 | | 3/2016 | |
| CN | 105473182 | | 4/2016 | |
| CN | 107492090 | | 12/2017 | |
| CN | 107708808 | | 2/2018 | |
| CN | 107715314 | A | 2/2018 | |
| CN | 107809980 | | 3/2018 | |
| CN | 108550156 | | 9/2018 | |
| CN | 109069858 | | 12/2018 | |
| CN | 113226459 | | 8/2021 | |
| EP | 3673955 | | 7/2020 | |
| KR | 20180060968 | A * | 10/2017 | G16H 50/70 |
| WO | WO-2011070461 | A2 * | 6/2011 | G06F 19/321 |
| WO | WO2018205922 | A1 | 11/2018 | |
| WO | WO-2018222755 | A1 * | 12/2018 | A61B 5/055 |
| WO | 2020136028 | | 7/2020 | |

OTHER PUBLICATIONS

Verhage, R. et al "PO-1021: Implementation and clinical use of a digital log regarding the Traffic Light Protocol in daily IGRT," Radiother. Oncol., vol. 119, pp. S494-S495, Apr. 2016.

Moller, Dltte Sloth et al "Adaptive Radiotherapy of Lung Cancer Patients with Pleural Effusion or Atelectasis", Radiotherapy and Oncologyi vol. 110, 2014, pp. 517-522.

Kwint, Margriet et al "Intra thoracic anatomical changes in lung cancer patients during the course of radiotherapy," Radiotherpy and Oncology, vol. 113, No. 3, pp. 392-397, Dec. 2014.

Elsayad, Khaled et al "Cone-Beam CT-guided Radiotherapy in the Management of Lung Cancer", Strahlenther Oncology, vol. 192, 2016, pp. 83-91.

Braun, Lore Helene et al "Resolution of Atelectasis during Radiochemotherapy of Lung Cancer with Serious Implications for Further Treatment. A Case Report", Clinical and Translational Radiation Oncology, vol. 9, 2018, pp. 1-4.

De Crevoisier, Renaud et al "Daily versus weekly prostate cancer image-guided radiotherapy A phase 3, Multicenter, randomized trial", Journal of Clinical Oncology, vol. 36, No. 6, 2018.

Lecun, Y. et al "Gradient-Based Learning Applied to Document Recognition", Proceedings of the IEEE, 86(11):2278-2324, Nov. 1998.

"Kumar, Pulkit et al Boosted Cascaded Convnets for Multilabel Classification of Thoracic Diseases in Chest Radiographs," ArXiv171108760 Cs, Nov. 2017.

Rajpurkar P. et al, "CheXNet: Radiologist-Level Pneumonia Detection on Chest X-Rays with Deep Learning," ArXiv171105225 Cs Stat, Nov. 2017.

Wei, Ran et al "A CNN Based Volumetric Imaging Method with Single X-Ray Projection", IEEE Instrumentation and Measurement Society, 2017.

Foote, Markus D. et al "Real-Time Patient-Specific Lung Radiotherapy Targeting using Deep Learning", First Conference on Medicla Imaging With Deep Learning, 2018.

Varfalvy, Nicolas et al "Classification of changes occurring in lung patient during radiotherapy using relative y analysis and hidden Markov Models", Medical Physics, vol. 44, No. 10, Oct. 2017.

International Search Report and Written Opinion of PCT/EP2019/085212, dated Feb. 25, 2020.

Mackay, D.J.C. Information Theory, Inference, and Learning Algorithms, Cambridge University Press, 2003.

"International Application Serial No. PCT EP2019 085212, International Preliminary Report on Patentability mailed Jul. 8, 2021", 7 pgs.

"European Application Serial No. 18215837.8, Extended European Search Report mailed Jun. 13, 2019", 7 pgs.

"European Application Serial No. 18215837.8, Noting of loss of rights mailed Feb. 3, 2021", 2 pgs.

"Chinese Application Serial No. 201980085849.4, Office Action mailed Oct. 26, 2023", w English Translation, 11 pgs.

* cited by examiner

AUTOMATED DETECTION OF LUNG CONDITIONS FOR MONITORING THORACIC PATIENTS UNDERGOING EXTERNAL BEAM RADIATION THERAPY

CROSS-REFERENCE TO PRIOR APPLICATIONS

This application is the U.S. National Phase application under 35 U.S.C. § 371 of International Application No. PCT/EP2019/085212, filed on Dec. 16, 2019, which claims the benefit of European Patent Application No. 18215837.8, filed on Dec. 24, 2018. These applications are hereby incorporated by reference herein.

FIELD OF THE INVENTION

The invention relates to a computerized system for radiation therapy support, to a computer-implemented method for radiation therapy support, to a method of training a machine learning component for used in the computerized system, to a computer program element, and to a computer readable medium.

BACKGROUND OF THE INVENTION

In external beam radiation therapy (EBRT) of, for example, thoracic malignancies, or other anatomical changes and lung medical conditions appearing during the course of the treatment are monitored, measured, and recorded. These records trigger protocols and decisions on the ongoing treatment. Currently, lung tissue changes and lung conditions are monitored and detected using visual inspection of CBCT (cone beam computed tomography) images.

However, visual inspection is error prone and time consuming. Visual interpretation and diagnosis of lung conditions is a specialized skill requiring extensive training. What is more, RTTs (radiation therapy technicians) are trained to recognize only a limited number of lung conditions. Less frequently appearing lung conditions, which could be detected by an experienced radiologist, might not be recognized by RTTs.

Also, frequent acquisition of CBCTs is associated with increased risk of developing secondary cancer. In order to reduce image interpretation burden on staff, and the total dose exposure to patients under treatment, clinics implement protocols based on images that are weekly acquired instead of daily. However, medical conditions that may develop in the interval between the weekly CBCT acquisitions may not be detected.

SUMMARY OF THE INVENTION

There may therefore be a need for systems and methods to address the above mentioned needs.

The object of the present invention is solved by the subject matter of the independent claims where further embodiments are incorporated in the dependent claims. It should be noted that the following described aspect of the invention equally applies to the to a computer-implemented method for radiation therapy support, to a method of training a machine learning component for used in the computerized system, to a computer program element, and to a computer readable medium.

According to a first aspect of the invention there is provided a computerized system for radiation therapy support, comprising input interface for receiving an input image acquired by an imaging apparatus, the input 2D projection image representing at least a region of interest ("ROI") internal of a patient and acquired before delivery of a dose fraction by a radiation therapy delivery apparatus, wherein the imaging apparatus is part of the radiation therapy delivery device;

a pre-trained machine learning unit ("MLU") configured to process the input image to detect a medical condition including a side effect caused by radiation therapy treatment (such as a secondary malignancy); and a communication component configured to provide, based on the detected medical condition, an indication for one or more clinical actions to be performed in relation to the patient.

The MLU is a processing unit, arranged in soft- and/or hardware implementing a machine learning ("ML") algorithm, based on machine learning model. In embodiments, the machine learning unit is arranged in a neural network architecture. Specifically, in embodiments, a convolution neural network (CNN) is used but. However other ML models such as support vector machines, decision trees, etc, are also envisaged.

As proposed herein, the input image is processed by the machine learning component before delivery of a radiation dose fraction. A single input image at a time may be sufficient as input for the MLC to detect the medical condition. No image pairs, or difference images, are required.

The indication may be provided in text, image, graphical, visual, audio or other form. The indication may be implicit and may then include automatically performing the action or at least initiating the one or more actions.

In embodiments, the patient is associated with a treatment plan, and at least one of the one or more actions as indicated by the reporting component includes an adaptation of the treatment plan.

In embodiments, the one or more actions include re-imaging the patient using a different imaging apparatus or modality. In particular, the imaging apparatus is a 2D imager, such an in-room kV projection imager or other, whilst the different imaging apparatus or modality is a 3D imaging apparatus as a CT scanner, CBCT, or U-arm imager.

In embodiments, the providing of the indication for the one or more clinical actions by the communication component includes transmitting a message through a communication network to a recipient. The message may be alert message sent to clinical staff on their phone, or other end-point-device. The communication component may present the outcome in form of probabilities of presence of a medical condition.

In embodiments, the system includes a visualizer configured to form an enriched image including the input image and a graphical rendering of a location in the image in relation to the detected medical condition. In embodiments where a NN model is used, a CAM (class activation map) may be formed and this may be fused with the input image. The CAM is produced in embodiments as a color map indicating the area most indicative of the medical condition in the input image. In embodiments, the outcome, that is, the detected medical condition, may be visualized by generating a color map indicating the areas of high probability as a projection on the input X-ray image.

In embodiments, the system is implemented by one or more processors configured for parallel computing, such as a GPU, TPU or other.

In embodiments, the imaging apparatus is included in the radiation therapy delivery device, such as LINAC, synchrotron or cyclotron, or other.

In embodiments, the input image is a 2D projection image, but 3D imagery may also be used in alternative embodiments, where available. The 2D projection image may be a non-diagnostic one, as this type of imagery has been found to be sufficient for present purposes and has in general lower dose cost than diagnostic imagery.

In embodiments, the system comprises a correlator component configured to correlate patient data and the detected condition with a treatment outcome value, indicative of a probability of a treatment outcome to be expected in relation to the patient. "Treatment outcome" as used herein in embodiments includes oncological outcome or side effects outcome. Oncological outcomes are related to success of failure of eradicating cancer (e.g., disease free survival at 5 years after treatment, local relapse of disease after 2 years). A side effects outcome means any side effect that the patient might develop after receiving radiotherapy treatment (pneumonitis, difficulty swallowing, etc. . . . ).

In embodiments, the system comprises a knowledge builder component configured to populate, into a data repository, patient data in association with the detected condition.

In embodiments, the organ of interest is at least one of the lungs of the patient but other anatomical ROIs are also envisaged.

In another aspect there is provided an arrangement, comprising a system as per any one of the previous claims and the radiation therapy delivery device and/or the imaging apparatus.

In another aspect there is provided an, a computer-implemented method for radiation therapy support, comprising:

- receiving an input 2D projection image acquired by an imaging apparatus, the input image representing at least a region of interest internal of a patient and acquired before delivery of a dose fraction by a radiation therapy delivery apparatus, wherein the imaging apparatus is part of the radiation therapy delivery device;
- processing the input image by a pre-trained machine learning unit to detect a medical condition, including a side effect caused by radiation therapy treatment; and
- providing, based on the detected medical condition, an indication for one or more clinical actions to be performed in relation to the patient.

In other aspect there is provided a method of training a machine learning model to obtain a machine learning unit according to any one of the previous claims. The training method includes receiving training data. The training data is applied to a machine learning model. The machine learning model produces training output. Based on the training output, one or more parameters of the ML model are adjusted, to obtain a pre-trained machine learning component. The adjustment may be done repeatedly, in one or more iteration cycles for a given training data item and/or for a plurality of training data items.

The training may be repeated with new training data or training may be a one-off operation. Transfer leaning is particularly envisaged herein where parameters from other, already trained models are used to initialize the instant model. In embodiments, transfer learning may be used. In transfer learning, parameters from ML models pre-trained on other image data may be used. This allows addressing a possible lack of existing training sets for radiation therapy. For instance, in RT the patient is usually lying. However, it has been found that standard chest x-ray imagery, acquired with patients standing, can be used as training images for present RT purposes. The ML component so trained has been found by Applicant to yield good results when provided, during deployment, with input images acquired with the patient lying.

In other aspect there is provided a computer program element, which, when being executed by at least one processing unit, is adapted to cause the processing unit to perform the computer-implemented method for radiation therapy support or the method of training the machine learning component.

In other aspect there is provided a computer readable medium having stored thereon the program element.

The proposed system may be used in external beam radiation therapy, and in particular in clinical decision support in radiation therapy planning, in particular for thoracic patients or other patients/lesions.

The proposed system provides an automated intra-treatment workflow trigger based on imaging data, preferably acquired in the RT delivery room.

In embodiments, the proposed system is configured to detect medical condition(s) before the delivery of the treatment fraction, thus allowing medical staff to act before delivering a fraction that might harm or aggravate the detected condition. Specifically, in embodiments, the invention proposes a system to automatically detect lung conditions using daily acquired planar projection X-ray images. The radiation dose from the acquisition of one planar X-ray is much smaller and using daily images would allow timely detection and application of clinical protocols aimed to manage these conditions. Moreover, detection of a lung condition in a planar X-ray image could trigger a warning to acquire a CBCT for further verification and validation.

Current protocols are based on visual inspection of CBCT images. To reduce the total dose to patients under treatment, some clinics implement protocols based on weekly acquired CBCTs instead of daily acquired CBCTs. However, under this protocol, conditions that develop in the interval between the weekly CBCT acquisitions cannot be detected. For example, atelectasis (collapsed lung) is a condition that can appear or disappear within very few days and with major consequences on the dose to regions of interest. Moreover, daily CBCT acquisitions are associated with an increase in staff burden, costs, treatment time, and in the risk of developing secondary cancer after RT. It is expected that a proposed system allows clinics to reduce the number of unnecessary CBCTs, reduce costs, patient and staff burden, and also reduce the risks of secondary malignancies.

The system may also provide automated treatment modification based on detection of complications and/or a trigger for further 3D CBCT acquisition.

Compared to manual visual interpretation of imagery, the proposed system can be used to reduce the time needed to visualize and detect medical conditions reduce inter-observer variability, and help detect conditions that the RTTs were not trained to recognize. In addition, the hospital could save expenses by minimizing the RTT training time.

Although the proposed system is envisaged to operate on 2D projection images, such as radiographs, the system may also be trained and used for 3D image data, such as CBCT, MRI or other. For instance, CBCT or other 3D image material may become available as a matter of course in other protocols or workflows. The proposed may also be useful to analyze retrospective image studies, such as CBCT, etc.

The proposed system and method can be used with all kinds of RT, such as photon therapy, but also particle RT or ion beam therapy, such as proton RT, carbon ion RT, and others. Also IMRT (Intensity-modulated radiation therapy), VMAT (Volumetric modulated arc radiotherapy) and other forms of treatment delivery are envisaged.

Definitions

As used herein, the phrase "providing an indication for an action" includes in embodiments, automatically initializing the respective action, in which case the indication is implicit rather than explicit.

- "user" relates to a person, such as medical personnel or other, operating the imaging apparatus or overseeing the imaging procedure. In other words, the user is in general not the patient.
- "3D" is shorthand for three-dimensional and "2D" is shorthand for two-dimensional.

In general, the "machine learning component" is a computerized arrangement that implements a machine learning ("ML") algorithm. A machine learning algorithm is configured to perform a task. In an ML algorithm, task performance improves measurably after having provided the arrangement with more training data. The performance of the ML in delivering the task may be measured by objective tests when feeding the system with test data. The performance may be defined in terms of an error rate for the task and test data. See T. M Mitchell, "*Machine Learning*", page 2, section 1.1, McGraw-Hill, 1997.

BRIEF DESCRIPTION OF THE DRAWINGS

Exemplary embodiments of the invention will now be described with reference to the following drawings wherein:

FIGS. 1,1A show a schematic block diagram of an arrangement for radiation therapy;

DETAILED DESCRIPTION OF EMBODIMENTS

Radiation therapy (RT), in particular external beam radiation therapy (EBRT), is a mode of treatment of cancer in animal or human patients.

RT is best thought of as a process in terms of a workflow with certain steps being performed over time. Initially, RT starts with a diagnosis of cancer which usually involves drawing together by clinical professional all available data about the patient, including image data. This (initial) data image data is obtained by using suitable medical imaging devices implementing imaging techniques such as emission imaging (eg, PET/SPEC) or transmission imaging, or other imaging techniques such as MRI (magnetic resonance imaging), or a combination of any of these. Example of transmission imaging envisaged herein includes X-ray based tomography, CT (computed tomography). Like MRI, CT can generate 3D imaging, which is preferred for precise location of a lesion such as a tumor.

Specifically, based on this initial image data, the area to be treated is localized and delineated, preferably segmented, manual or automatically, or both.

Based on the location and spatial extent of the tumor area (referred to herein as the region of interest, ROI) and heeding the organs of risk surrounding the ROI, a treatment plan TP is drawn up for the patient. Drawing up the treatment plan may include running an optimization algorithm on a computing unit to compute the required dose of radiation to be deposited at the region of interest for effective treatment, and possibly, different spatial directions along which some or all of the radiation dose is to be delivered to the ROI. The optimization is configured to balance the two opposing objectives to harm as much of the cancer tissue as possible whilst at the same time spare as much of the surrounding healthy tissue as possible. Given the treatment plan, the RT work flow enters the therapy delivery phase.

Broadly, therapy delivery includes operating a radiation therapy delivery device RTD. The radiation delivery device RTD is configured to generate a high energy radiation beam (in the region of MV) to effect the treatment. Requirements in the treatment plan TP are translated into a control program that controls the radiation therapy device RTD, that is, the manner in which the radiation is delivered by the radiation delivery device RTD. The total radiation dose cannot usually be delivered at once in full. The delivery of the total dosage is therefore broken up as per the treatment plan TP into partial dosages called fractions. The fractions are delivered in separate sessions over time, during the course of days or weeks, usually at regular intervals such as daily, possibly interrupted by rest phases where no radiation is delivered such as during the weekend or in any other arrangement.

Figure 1:
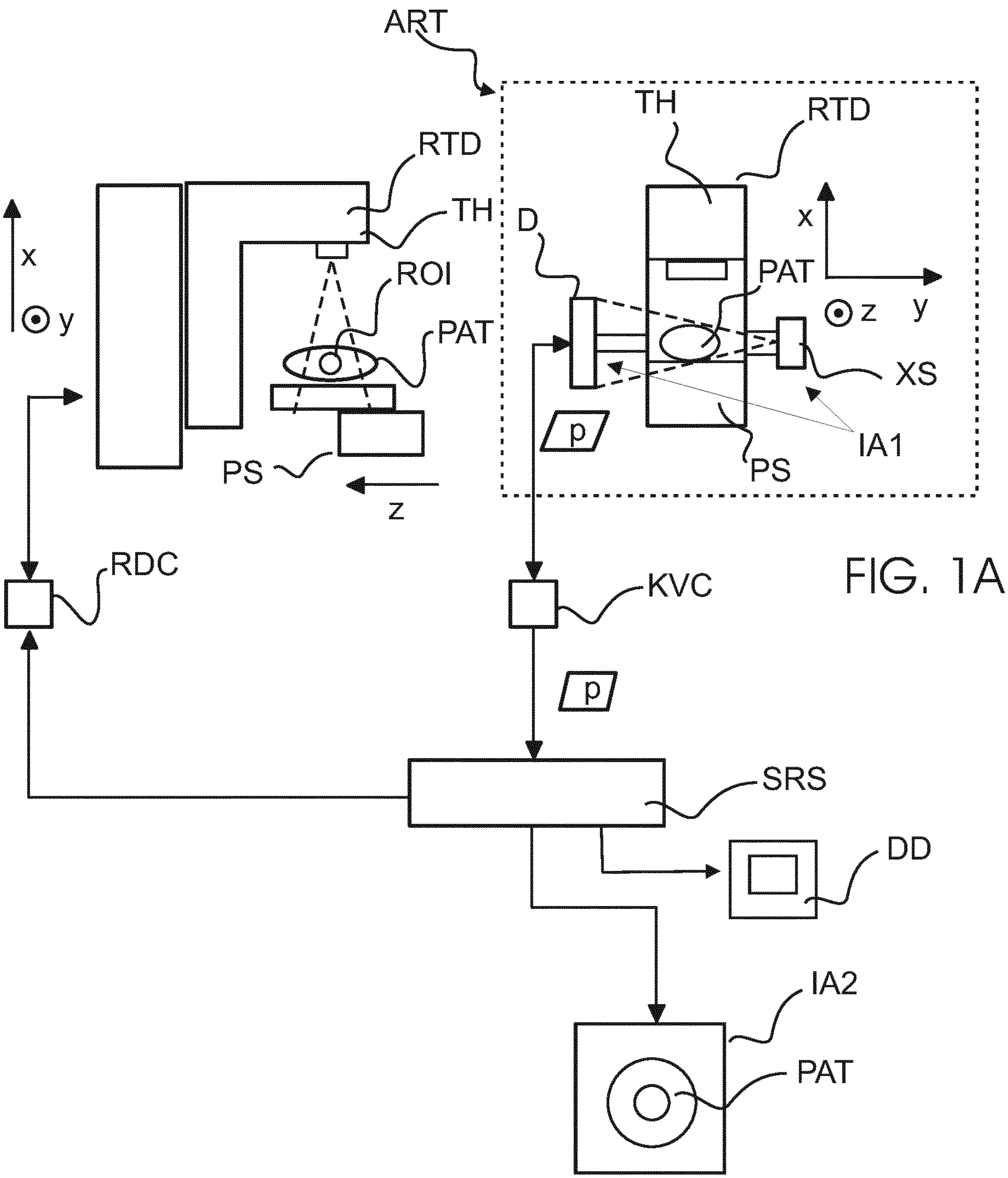

Turning now in more detail to FIG. 1, this shows an arrangement ART for radiation delivery given a treatment plan TP for patient PAT. The arrangement includes the radiation delivery apparatus RTD situated in a treatment room at a medical facility. The radiation therapy delivery device RTD may be any one of a linear accelerator or LINAC or a cyclotron/synchrotron, depending on the type of radiation to be delivered. Photon based radiation delivery is usually done by a LINAC, whilst for radiation made up of other particles such as protons or ions, such as carbon ions, a cyclotron/synchrotron apparatus is used.

Purely for example's sake, we will on occasion refer to the LINAC as an exemplary embodiment, with the understanding that the other types of radiation delivery apparatus are specifically envisaged herein in alternative embodiments. In particular, the following is not tied to linear accelerator based treatment.

Broadly, the LINAC includes, mounted in the treatment room, a rotatable gantry. On the gantry there is mounted a treatment head TH. During treatment the patient resides on a patient support PS such as a bed. The region of interest, ROI, to be treated is exposed to treatment beam TB emitted by the treatment head upon energizing same. In the treatment head, accelerator equipment operates to accelerate relevant particles such as electrons or others released from a source to generate the treatment beam.

The treatment head TH in the gantry is configured to rotate, not necessarily in a full rotation, around the region of interest to deliver the radiation or the given fraction from different directions. In embodiments, a beam forming tool such as a multi-leaf collimator or other may be used to conform the treatment beam's cross section, in shape and/or size, to the shape of the region of treatment as seen from different perspectives from different directions.

The left hand portion of FIG. 1 shows a schematic drawing of the LINAC in side elevation whilst inset figure, Figure LA in the right hand portion of FIG. 1 shows a frontal view along the longitudinal axis Z of the patient.

Control of the operation of the LINAC is through a computerized control unit RDC. The RDC is communicatively coupled to one or display devices that allow clinical personnel, such as a radiation therapy technician RTT, to oversee and monitor the ongoing treatment session.

Control unit RDC receives, in particular, the control program computed for the given treatment plan and the fraction to be delivered. The control program may include setting parameters that help achieve the fraction dosage and how this dosage is to be delivered from, possibly, different spatial directions around the region of interest. Specifically, the control program may include control commands to re-position the treatment head relative to the region of interest and optionally includes commands to operate the beam forming tool accordingly. The control program also includes parameters to adjust the LINAC for the correct energy setting to produce the treatment beam at the correct energy to deliver the required fraction dose. The program may be loaded into the control unit RDC. The unit RDC executes the program and interfaces with circuitry in the LINAC to put the radiation delivery into effect whilst the patient resides on the patient support correctly positioned.

During the course of the treatment delivery period in the different sessions, further control imaging may be performed in order to monitor how the patient and the tumor is responding to the treatment. Possible responses that may be encountered are that the tumor is not responding at all, which is undesirable, or that the tumor does respond. The response of the tumor may include shrinkage of cancer tissue but may also mean in circumstances that the tumor is still growing etc. Furthermore, because of the hazardous nature of the treatment beam, the patient may develop treatment related side effects.

The control imagery is preferably obtained daily or once per week or at any other schedule, depending on the requirements. The control imagery is obtained in embodiments by a control imager IA1. Preferably, as envisaged herein, the control imager IA1 includes an in-room kV imaging apparatus IA1. "in-room" referrers to the control imager IA1 being arranged in the treatment room together with the RTD or that the control imager may is movable into the treatment room. Specifically, the control imager IA1 may be arranged as a permanent fixture in the treatment room, just like the LINAC, or may be mobile, so can be moved into the room, on wheels or tracks or other, when required.

Specifically, the in-room imaging apparatus IA1 may be integrated into the LINAC as shown in FIG. 1A. In exemplary embodiments, two robotic arms or other attachment means may hold respectively an x-ray source XS and an x-ray sensitive detector D opposite the x-ray source XS as schematically indicated in FIG. 1A. In order to acquire the control imagery, the x-ray source XS is energized to produce an x-ray beam for imaging. The x-ray beam XB has a lower energy level than the treatment beam. The imaging beam may be in the region of kV as opposed the treatment beam which is at least in the MV energy region. The X-ray beam is emitted from the source XS and passes through the patient. The imaging beam is modified by tissue in the patient and the modified beam is then detected at the detector D. An imaging processing module then translates the detected signals at the detector into a control image p. Preferably, the control imaging apparatus IA1 is a 2D radiography system. In other words, the control image p produced is a projection image. A controller unit KVC controls operation of the control imager IA1, such as the in-room kV imaging apparatus.

As mentioned, the control imager IA1 is preferably, but not necessarily, situated in the same room as the radiation therapy device RTD. The control imager IA1 may not necessarily be integrated physically with the LINAC as shown in FIG. 1A but may instead be mounted as a separate unit on tracks or wheel for instance, so that it can be moved in the treatment room, positionable at the patient PAT, whenever control imaging is required. In other embodiments, the control imager IA1 is ceiling-, floor-, or wall-mounted or mounted on a stand, or other in the treatment room. In other embodiments, the control imager IA1 may be arranged on rollers or tracks as a mobile device and can be moved from another room into the treatment room as required.

In order to better support the radiation treatment during the different fractions, the arrangement ART includes a computerized radiation support system SRS referred to herein as the "SRS". The envisaged SRS can better support the treatment because it is configured to automatically screen the control imagery p for a medical condition which may have developed due to exposure to the treatment beam TB itself. The screening by the SRS of the input image for medical conditions may be done quicker and more accurately than a human clinician.

As envisaged herein, the control imagery is acquired before delivery of a given fraction dose by radiation delivery device RTD. The pre-fraction control image p is then analyzed by the support system SRS. An outcome of the analysis of the input imagery p by the SRS is then indicated on a display device DD, for instance visually, in text form or in audio or other, or in combination of some or all of the foregoing. The SRS outputs one or more indications for one or more clinical actions to be taken based on the detected medical condition. The indication of the said actions may also include initiating the said actions. Actions envisaged include, for instance, producing an alert signal once a medical condition has been detected. The alert signal may be a visual signal or an audio signal or a combination. In embodiments, for instance, the SRS may be coupled to a transducer such a warning lamp or a loudspeaker. Thereby the SRS can cause a warning light to flash or give otherwise visual signals and/or to have an alarm sounded out through the speaker system. Other actions will be discussed below more fully.

Figure 2:
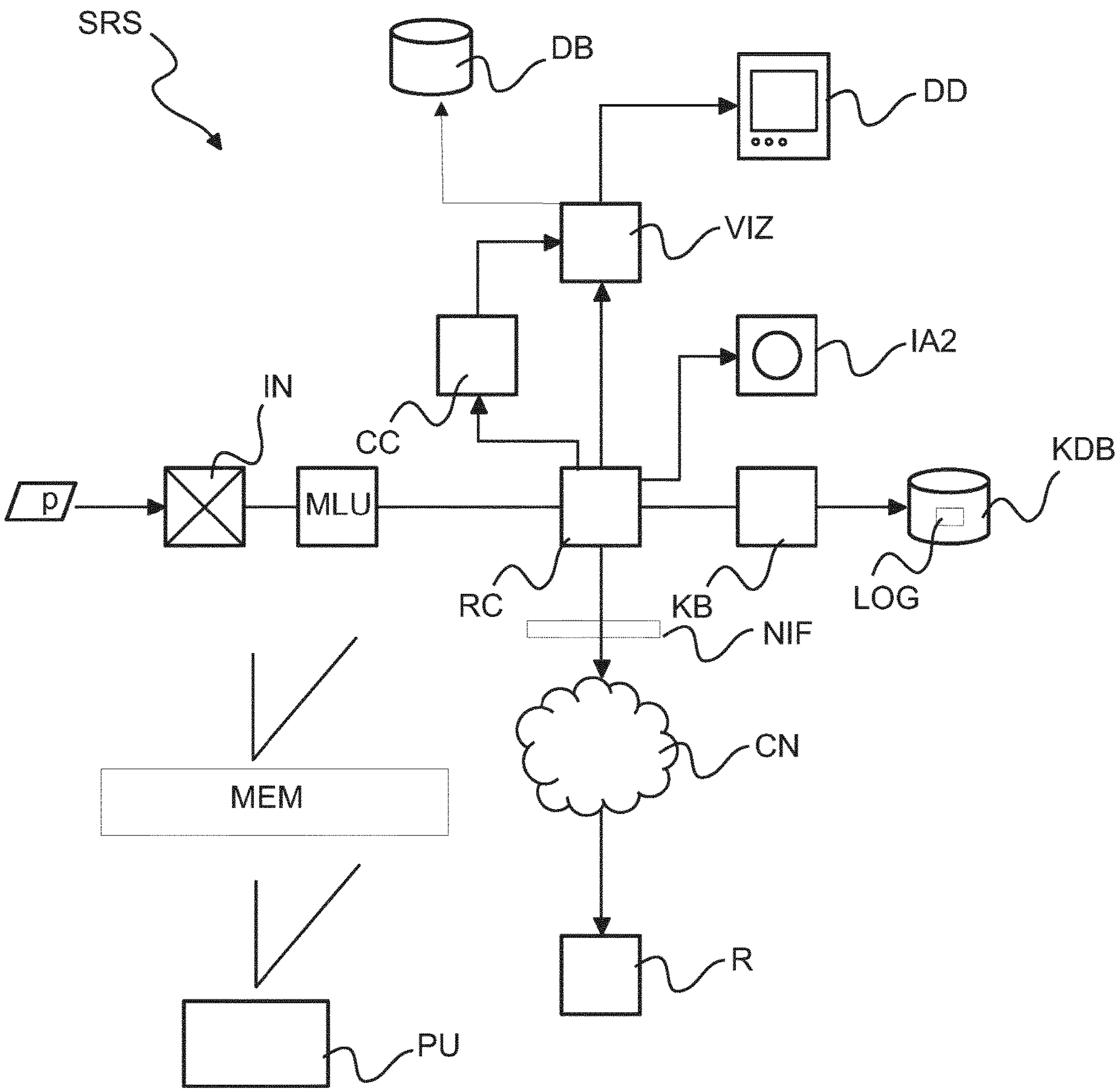
FIG. 2 shows a block diagram of a computerized system for supporting radiation therapy.

Reference is now made to FIG. 2, a schematic block diagram, providing more details on the computerized RT support system SRS and, in addition, provides more details on the envisaged actions indicated or to be taken by the SRS as envisaged in embodiments.

Components of the SRS as shown in FIG. 2 may be arranged in one or more memories MEM, distributed or central. The SRS may be implemented by a single processing unit PU or by a plurality of such processing units in a distributed computing environment such as in a Cloud architecture or otherwise.

Preferably, the SRS includes a machine learning unit MLU pre-trained on a corpus of training imagery. There is also a reporting component RC that acts based on output from the machine learning unit MLU.

The machine learning unit MLU may be implemented preferably by a neural-network architecture, for instance a convolutional neural-network architecture CNN. However, other machine learning models may also be used, such as support vector machines, regression models, decision trees and others. Preferably, the model is trainable, that is, the model improves performance when trained with training imagery in a training procedure. Once trained, the machine learning unit MLU may be used in deployment mode where it processes new imagery p from a given patient. In other words, the MLU is operable in two modes, in training mode and in deployment mode.

Focusing in the following first on the deployment mode, this includes receiving the control imagery p through input port IN. The control imagery p is acquired before delivery of the instant fraction. In a preferred embodiment, the input image p is in particular a 2D projection image acquired by the in-room KV imaging apparatus or similar.

Input image p is then processed by the machine learning unit before delivery of a planned fraction. The machine learning unit MLU processes the input control image p to produce output data at its output interface (not shown in FIG. 2). The output includes indications for one or more of a pre-defined set of medical conditions. Specifically, in embodiments the MLU operates as a classifier to classify the input image p into one of a pre-defined plurality of classes, each class representing a different medical condition. Preferably, the output data is provided in a vector format but other data structures are also envisaged.

In more detail, in the neural-network arrangement of the MLU, during deployment, the input image p is applied to an input layer of the neuro-network. Pixels of the input image p are then propagated through the network in a manner to be described in more detail below to produce accumulated responses, numbers that is, that may be collected in respective entries of an output vector. Each index of the output vector represents a class, in this case a medical condition, and the accumulated responses represent, possibly after normalization, scores for the presence of the respective model condition represented, or "encoded", by the respective index i. The higher the number in a given entry for index i, the more likely it is that patient PAT presents with the respective medical condition i. The accumulated responses across the different entries may represent estimates of respective probabilities for the different medical conditions. In alternative embodiments, the output data may instead be supplied as a binary result, that is, outputting a name of the medical condition.

The reporting component RC then processes the output data, such as the output vector, as output by the ML to provide an indication for one or more medical actions to be taken in response to the detected medical condition. The said indications may include initiating the one or more actions. More than one medical conditions may be detected by the MLU.

Broadly, operation of the reporting component RC may include mapping the detected medical conditions onto clinical actions and/or interfacing, through suitable interfaces NIF, with suitable agents to carry out the actions and/or to inform the user about the actions. In more detail, a detected medical condition as produced by the MLU is mapped by the reporting component RC to an indicator such as an index, identifier for a clinical action, such as treatment suggestion. The mapping may be based on or more clinical actions as prescribed by known medical protocols. The protocols and their references to associated medical actions may be implemented as entries in a medical database. The mapping by the RC may be implemented by suitably configured database querying interfaces. For example, the detected medical condition may be "pneumonia" which may mandate, as an associated medical action, the taking of the patient's temperature.

The medical actions may be indicated on a graphics display generated by a visualizer VIZ and rendered for display on the display device DD. The graphics display may include textual or icon widget information associated with the suggested medical action. In embodiments, the graphics display may be generated in form of a GUI. The GUI may include icon widget(s), interactive graphical user interface elements, which enables the user to initiate the indicated action, eg booking a necessary medical equipment etc.

In addition or instead to indicating the medical actions on the graphics display as described, an alert transducer may be operated once a medical condition is detected, or if a certain type of medical condition is detected that is deemed to require immediate medical attention. Operating a transducer (not shown) may include operating a warning light arranged for instance in the treatment room and/or in a RT operation control room outside the treatment room, or elsewhere in the medical facility. In addition or instead, the transducer is arranged as a speaker system. An alarm may be sounded out through the speaker system if a medical condition or a specific type of medical condition with sufficient severity is detected by the MLU.

The reporting component may also include a network communication interface NIF to communicatively couple with a communication network CN, such as an intercom system, or other. A message in relation to the detected medical condition may be sent to the recipient R. Recipient R may include an endpoint device such as a laptop, phone, pager or any other device of medical staff to inform them of the detected medical condition. For instance, an email or short text message (SMS) may be sent to the phone of the responsible clinician.

In embodiments, one of the actions suggested by the reporting component may include a recommendation to have the patient re-imaged with the additional, higher dose, 3D imaging apparatus AI2, such as a CBCT. In this way, the use of the CBCT may be reduced. The CBCT is only used for reimaging when the medical condition is actually detected. The proposed SRS hence obviates the need to have the patient daily imaged with a high dosage imaging apparatus such as the CBCT. The daily image based monitoring can be done by the in-room KV imaging apparatus IA1 that operates at a much lower dose. Because of the higher sensitivity and accuracy of the pre-trained machine learning unit MLU, the possible presence of a medical condition may be established using lower dose incurring 2D projections. No resort needs to be taken to higher dose incurring 3D imaging apparatus for the purpose of acquiring periodic (eg, daily) control images.

It will be appreciated that any of the above mentioned actions are indicated or actions initialized only once a respective class probability, an entry in the output vector, exceeds a fixed or user-definable trigger threshold q. For instance, q may be set as at least 50% but this may be too conservative, so a higher trigger threshold may be set at, for example 60% or 75% or 80%, or other.

In embodiments the reporting components RC may be further configured to interface with a knowledge builder module KB to populate the output as produced by the MLU into a medical data base KDB. In particular, a data base record is created automatically including patient's data and the indication for the detected medical condition. The patient's data may include data that characterize the patient, including in particular biometric data, such as weight, age, height, etc. Optionally, it is also a time stamp that is included into the record, the time step indicating the time and/date when the medical condition was so detected by the MLU. In this manner, over the course of time and patients treated, a knowledgebase can be created that may help in further evaluating or optimizing treatment at the given medical facility.

Additionally, or instead, the reporting RC may be configured to automatically update, preferably for each fraction, an electronic logbook LOG of the given patient. Manual input of the results by staff as previously done is no longer necessary.

In embodiments the system SRS may further or instead to the above include a correlator component CC. The correlator component CC correlates patient's data and the detected medical condition with a treatment value score. This score or value indicates a probability of a treatment outcome. The treatment outcome relates to oncological outcome or side effects outcome. Oncological outcomes are related to success of failure of eradicating cancer (e.g., disease free survival at 5 years after treatment, local relapse of disease after 2 years). A side effects outcome means any side effect that the patient might develop after receiving radiotherapy treatment (pneumonitis, difficulty swallowing, etc. . . . ). This information on treatment outcome may be mapped to the number of expected work flow steps to be performed for the given patient. The correlator component is preferably itself arranged as a machine learning component and separately pre-trained on a suitable data set. The predicted, correlated, treatment score values may be stored in a database DB.

In embodiments, the visualizer VIZ of the SRS is configured to combine the output as produced by the machine learning unit MLU with the input image. This may be done in one embodiment by forming an enriched image that includes a class activation map (CAM) superimposed or overlaid on the input image p.

The CAM is a map that identifies image pixels in the input image p that contributed more than a given threshold to the medical condition as detected by the MLU in its finding. In particular, credit paths for the medical condition that garnered the highest probability in the output can be used to back-track through the network to find the pixels that contributed more than the pre-defined threshold to that outcome. The pixels so identified can then be rendered visually marked up in the input image to so form the CAM. The CAM allows the clinical staff to better locate spatially the anatomy affected by the predicted or detected medical condition.

Figure 3:
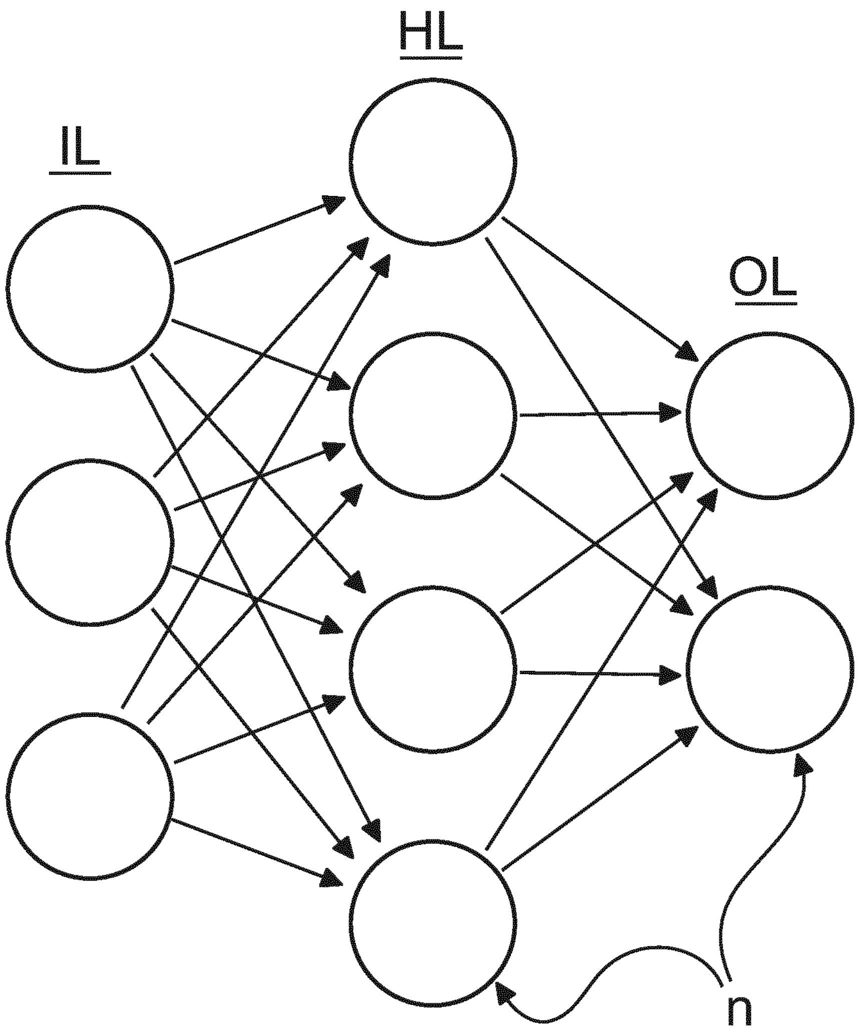
FIG. 3 shows a component of a machine learning unit in one embodiment.
Figure 4:
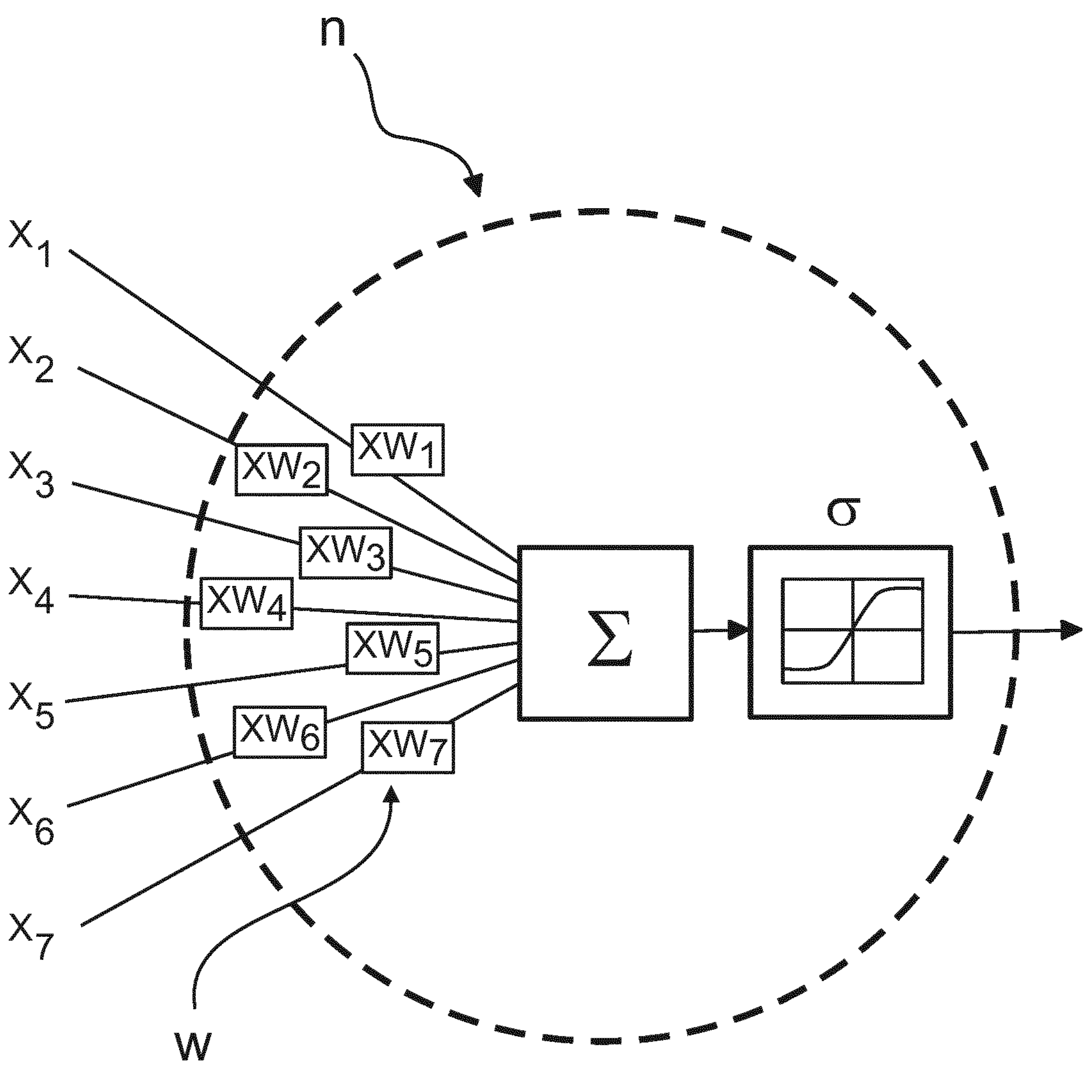
FIG. 4 shows a processing mode of a machine learning component according to one embodiment.

Reference is now made to FIGS. 3, 4 to describe the machine learning unit MLU in more detail and as envisaged herein in embodiments. More particularly, in some, but not necessarily all, embodiments, the machine learning unit MLU is arranged in a neural-network (NN) architecture. More particularly and in embodiments the neural-network NN is arranged as a convolutional neural-network CNN.

In embodiments as is shown in FIG. 3, a neural-network model M comprises a plurality of computational units, referred to herein as nodes "n", that are interconnected by edges. The edges represent information flow. A neural node can receive input from other nodes to which it is connected through respective edges and can produce an output on its own to connect to another node and so on. Preferably the nodes n are arranged in cascaded fashion in layers.

A node, all referred to as an "artificial neuron", in one layer can receive the output produced by nodes in a previous layer. An individual, single, node n is shown in schematic fashion in FIG. 4. It comprises a processing function Σ that processes inputs x's received by that node. In the example show, there are seven inputs $x_1$-$x_7$. The inputs received at the node are weighted by respective weights, numbers, $w_j$. In embodiments the processing function to summing the weighted inputs. Other functional expressions may also be used instead. The output of the processing function Σ is then passed on through an activation function σ, such as sigmoid function, softmax-function or other, hard or soft, thresholding function, to produce a node output which can then be processed as input at a node in a subsequent layer and so on. The output may be passed on to more than one node in the follow up layer. The nodal outputs are sometimes referred to herein as the response.

The layers may be represented, stored and processed as matrices of two or more dimensions, each entry representing a node. The nodes may pass on their respective outputs to nodes in a follow-up layer and so on. The first layer is called the input layer IL to receive the input image p. There is an output layer OL where the output is provided as classification onto the number or classes, each representing a respective medical condition, such a lung condition as mentioned above. In between the output and input layer there are a number of one, better 2 or more hidden layers HL.

The nodes in a given layer are not interconnected but are connected only to nodes in the follow up layer and nodes in the previous layer. Nodes between layers may be fully connected to the previous layer and/or follow up layer as shown in FIG. 3. In this case, the hidden layer HL represents a fully connected layer. In addition or instead, not-fully connected layers referred to as convolutional layers are also envisaged. Each node in such a convolutional layer receives as input output only from a sub-set ("receptive field") of nodes in the previous layer. Also, the edges for the receptive field may not be fixed but may change. Specifically, the receptive field is "scanned" over the previous layer to process respective different sub-sets of nodes of the previous layer to produce input to, respective, different ones of nodes in the next layer. The receptive field is similar to convolution kernels, hence the name convolution layer.

Other layer types envisaged herein include deconvolution layers that are approximations of the inverse of convolution layers. Yet other layers envisaged herein are pooling layers, drop-out layers, activation layers. Drop-out layers cancel edges between nodes from different layers and activation layers include additional soft or hard thresholding for example by using softmax-functions, sigmoid functions or other. Drop-out layers and activation layers help reduce overfitting by introducing non-linearities.

Some layers, such as convolution layers with stride (scanning step size)>1 or pooling layers reduce data dimension through down-sampling. Specifically, in such down-sampling layers, the number of input values received is larger than the number of output values that are output by those layers. Some layers, such as the deconvolution layers, are up-samplers that increase dimension, through interpolation-like operations.

A CNN may include any combination of the above mentioned layer types, with one or more repetitions. In embodiments, a series of one or more convolution layers arranged after the input layer and may be followed by one or more up-sampling layers such as deconvolution layers. Combinations of convolution layers are followed by combinations of deconvolution layers for instance. The CNN hence performs cascaded down-sampling and then cascaded up-sampling, or the reverse of this. Some or each of the convolutional or deconvolution layers, or layer of the other types, may have a separate activation layer to process their respective local outputs. In embodiments, the CNN essentially maps the imagery p, having size L×M in pixels, to a vector of length N, thus performing a dimensional reduction. N equals the number of distinct medical conditions into which the image p is to be classified. In embodiments, the length of the output layer vector OL is N+1, where one explicit class is added for a negative finding, "no medical condition". However, in embodiments no such extra negative class is added. In these embodiments, a negative finding is concluded is no class attracts accumulated responses that represent a fraction of more than the trigger threshold q.

To set up a neural-network model as envisaged herein, the number of hidden layers and their manner of processing, their type, such as convolutional, activation, deconvolution layer and so on, may be specified. In addition, the size of each layer, that is, the number of nodes in each layer, needs to be specified. As mentioned, the whole structure NN can be represented by a plurality of two or higher dimensional matrices and operations of the neural-network can be represented as matrix operations. The size, nature and sequence of layer defines the architecture of the NN. Furthermore, the NN model, CNN or other is parameterized by a set of network parameter NP. The NPs include in particular the weights w at each node as exemplified in FIG. 4. Further parameters may specify the activation function for each node etc. The number of network parameters may be in the order millions. Training the network amounts to adjusting the network parameters so that the network performs correct classifications during deployment.

Before the network NN can be trained, the parameters NP may need to be initialized for example by a random choice, by populating the parameters with constant values or indeed by using parameters from another pre-trained image classifying network. The latter approach is known as transfer learning and specifically envisaged herein in embodiments. Once the parameters have been learned in a training procedure based on training data, the machine learning unit is considered ready for deployment.

In deployment, the input image acquired in-room, before the next fraction, is received and applied to the input layer IL. The size of the input layer corresponds to the pixel size of the input image. In other words, the input layer is a matrix where each node is populated with a respective one of the pixel values of the input image. The pixel values are then propagated as input through the network now processed as described above by each of the nodes in each hidden layer to produce the output vector at the output layer OL. The vector OL may include numbers in each entry (some of which may be zero) that represent the respective accumulated response. In embodiments, the higher the number in an entry the higher the likelihood that the respective medical condition as indexed by that entry is present. The outputs collected in the output vector may be normalized by the number of total responses received. The so normalized vector than represents an approximation of a probability density over the set of medical conditions. The entry that garnered the highest number or highest fraction may then be considered the detected medical condition.

In a simpler embodiment, the vector may comprise only two entries for two given diseases although in practice a larger number of medical conditions may be of interest. For instance, in the lung or chest imaging at least four medical conditions are of interest include pneumonia and others. In the thoracic embodiment therefore the output vector has at least a length of four in embodiments, but classification into fewer classes may still be of interest in embodiments.

The reporting component CC may be configured to provide an indication only for the medical condition that has garnered the highest response. The indication may include visualization by visualizer VIZ on displayed device, in text form by displaying the name of the medical condition. Alongside the name, the probability may be indicated as a number. Alternatively, the whole output vector representing the probability density is visualized as a curve in the graphics display, with the horizontal axis listing the medical conditions by code or natural language name. In yet other embodiments, a thresholding will be applied to indicate for instance only the top k−(k>1)-estimates for the detected medical condition. In other words, rather than outputting an indication of a single medical condition, respective indications for a plurality of conditions is output, preferably ordered according to the perspective magnitudes in their output vector entries.

In some embodiments, for some or each of the identified lung conditions, a class activation map (CAM) is produced by the visualizer VIZ to generate a color or grey value map indicating an (image) area indicative, or most indicative, of the respective detected medical condition in the input image. In another embodiment, the CAM can be used to guide the user to the respective image area of detected disease in the projection radiograph. Alternatively, in another embodiment, the CAM can be projected on a 3D image acquired by the second imaging apparatus IA2. For instance, the CAM may be projected on, for example, coronal slices of the 3D CBCT allowing the user to quickly identify and confirm the detected medical condition(s) in the 3D image.

Figure 5:
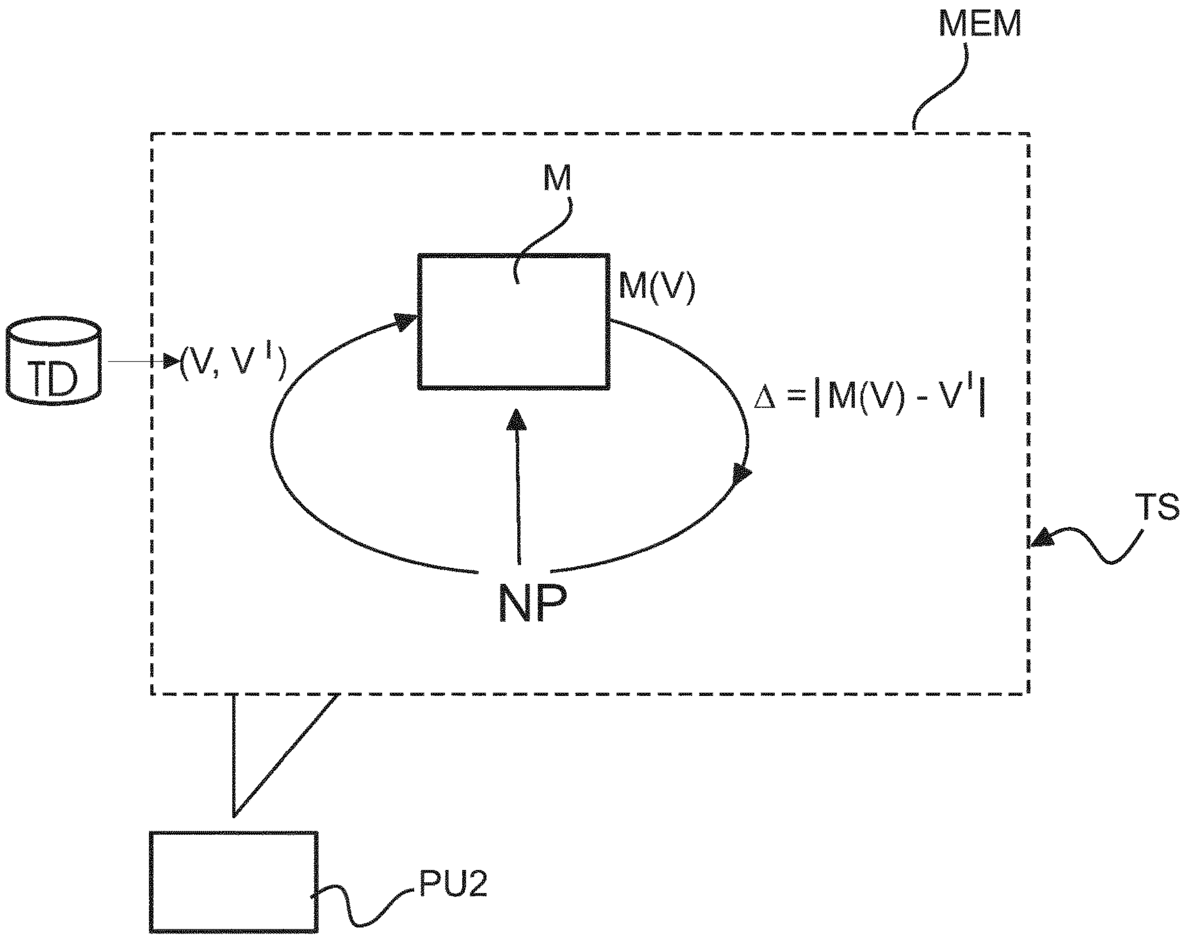
FIG. 5 shows a system for training a machine learning model.

Reference is now made to FIG. 5 that shows in schematic fashion a training system TS as envisaged in embodiments for training a machine learning component, in particular of the neural-network type.

A computerized training system TS may be preferably implemented by one or more processing units PU2 configured for parallel computing. As mentioned earlier, the NN-computations can be efficiently represented by matrix operations which can in turn be parallelized and quickly computed by such processors configured for parallel computing. Examples include graphics processing units GPU's (graphical processing unit) or TPU's (tensor processing units) as required. The network NN to be trained is specified by its architecture, initialized with a set of initial network parameters NP. The architecture and the network parameter NP represent a model M for the machine learning unit. Training of the network model M proceeds as follows. The processing unit PU2 to implement the training may or may not be different from the processing unit PU1 used for deployment. Preferably, but not necessarily, both are configured to parallel computing, such as GPUs and/or multicore systems and other.

Given a set of training data (on which more further below) this comprises pairs of data items, one being training input v and the other the target v' associate with the training input v. For instance, the training input image v may be a historical projection image of the patient whilst v', its target, represents a label for a medical condition known to be represented by the historical image. Preferably a large number of such labeled sets of training data is available as can be retrieved from medical records held in medical facilities.

Training data may be based on historical data held in the one or more memories MEM, such as in medical records of one or more hospital information systems HIS (hospital information system) or PACS (picture archive communication system). Specifically, the historical training data may be obtained from a medical data repository DB such as an Oncology information system ("OIS"). Imagery relevant for the anatomy of interest (lungs, heart, etc) and type of medical condition may be retrieved based on relevant information in DICOM header files of the image data or in annotations, possibly combined with information held in patient data records. The training data may be retrieved automatically by a scripting program run on a computing unit. The scripting program automatically interfaces with suitable database systems and searches automatically for the desired keywords, patterns in relation to the image and the associated medical condition. Using of existing metadata such as DICOM header identifiers and or other annotations, an explicit labeling may be avoided, making the procurement of training data quicker and more efficient.

During the learning phase, a framework is generated (on which more further below at FIG. 5) that is capable to predict the rate of plan adaptation incidents for the corresponding patient population. Once suitably trained, the MLC is ready for deployment and is now ready to receive the data for a currently treated number of patients to produce preferably graphical indications as for instance according to FIG. 3 or others.

The training data may be held in a repository TD, a database or other memory. For each pair v, v' of training data, the training input v is applied to the model M to produce an output M(v), in this case an identifier for the estimated medical condition. This output M(v) classification is then compared with the target v' label associated with the training input image v. The output MV should correspond to the respective target v'. However, in general there will be an error A. Based on the error A, the initial set of network parameters NP is adjusted in one or more iteration cycles to arrive at the final set of network parameters that define the model for the MLU.

In more detail, in embodiments, the training output M(v) may be represented as a vector ($c_1$, $c_2$, . . . , $c_N$), $0 \le c_1 \le 1$ of accumulated responses registered for the training input image v. This vector may be normalized. The target may be encoded as an indicator vector (0,0, . . . 1, . . . 0), N-long and having unity "1" at an entry that corresponds to the correct medical condition. The error A may then be formulated based on a suitable error measure $\Delta = \mu(M(v), v')$, such as the Euclidean distance, or squared Euclidean distance, between the two vectors ($c_1$, $c_2$, . . . , $c_N$) and (0,0, . . . 1, . . . 0). Alternatively, μ may be chosen as the squared Euclidean distance, or as any other $L^P$ norm, root-mean-square, or indeed any proximity measure. In embodiments, for the i-th training pair, $v_i$, $v_{i'}$. $\Delta = \Sigma_j (c_j - \varepsilon_i)^2$, $\varepsilon_i = 1$ at the relevant entry, and zero otherwise. It will be understood by those schooled in the art that the described numerical encoding in terms of vector entries is merely an exemplary embodiment, and that the particular numbers are mere examples (but still envisaged). Other encoding schemes, with other numbers may be used instead. It will be appreciated herein that the encoding, such as vector index i is to represent a certain medical condition, is, as such, an arbitrary semantic, but, once agreed, should be consistently maintained throughout the training or deployment.

The error depends on the current set of network parameters. A number of different numerical algorithms are envisaged to adjust network parameter adjustment NP to optimize, in this case minimize, the incurred error A. One group of such algorithms, such as called gradient-descent based algorithms, are configured to adapt the network parameters in an iterative fashion in one or more iteration cycles so that the error is minimized. The network parameters NP are updated during the iteration cycles, so that the error function Δ is minimized for all pairs v, v'.

In yet more detail, and in embodiments, the updating of the network parameters proceeds in two nested loops. In one loop, for a given fixed pair v,v' of training data, the network parameters are adjusted as described above. In this loop, the same input image v is applied again to the Model M, this time having the adjusted new parameters, to produce a new output M(v) which is again then compared with the target V, and so on for number of different iterations.

The learning algorithm then proceeds to the outer loop where another pair different from the first is processed in a similar way and the iteration proceeds over some or all pairs in the training set. A consolidated objective function F is taken for the aggregated errors A produced by each training data pair so that, at the end of the optimization, the network parameters are adapted to yield an optimal result for all the training data pairs in the training set for the consolidated error F. Specifically, the consolidated error F may be formulated as the sum over all error, as measured by μ, as $F = \Sigma_{v,v'} \mu(M(v), v'))$. The optimization algorithm is configured to minimize F.

At the conclusion of the training sequence, that is when the neural-network parameters have been adapted, the neural-network model is considered fully trained and this then represents the machine learning unit MLU that can be used as described above during deployment. The MLU can hence be applied to patient imagery p which was not part of the training corpus.

It will be understood, that the above described learning system TS may be formulated as a maximization in terms of a utility function, rather than as minimization of the error function as described above. Furthermore, it is not necessarily the case that a global optimum is found by the optimization algorithm. Instead, a local minimum may be found which is however sufficient in most cases. The iterations for the optimization may be run until a sufficient convergence to the global or local minimum is achieved. The iterations may be stopped once a proximity threshold is respected. Alternatively, iterations may be aborted earlier still, for example after a number of fixed iteration cycles, or as otherwise required and requested.

Figure 6:
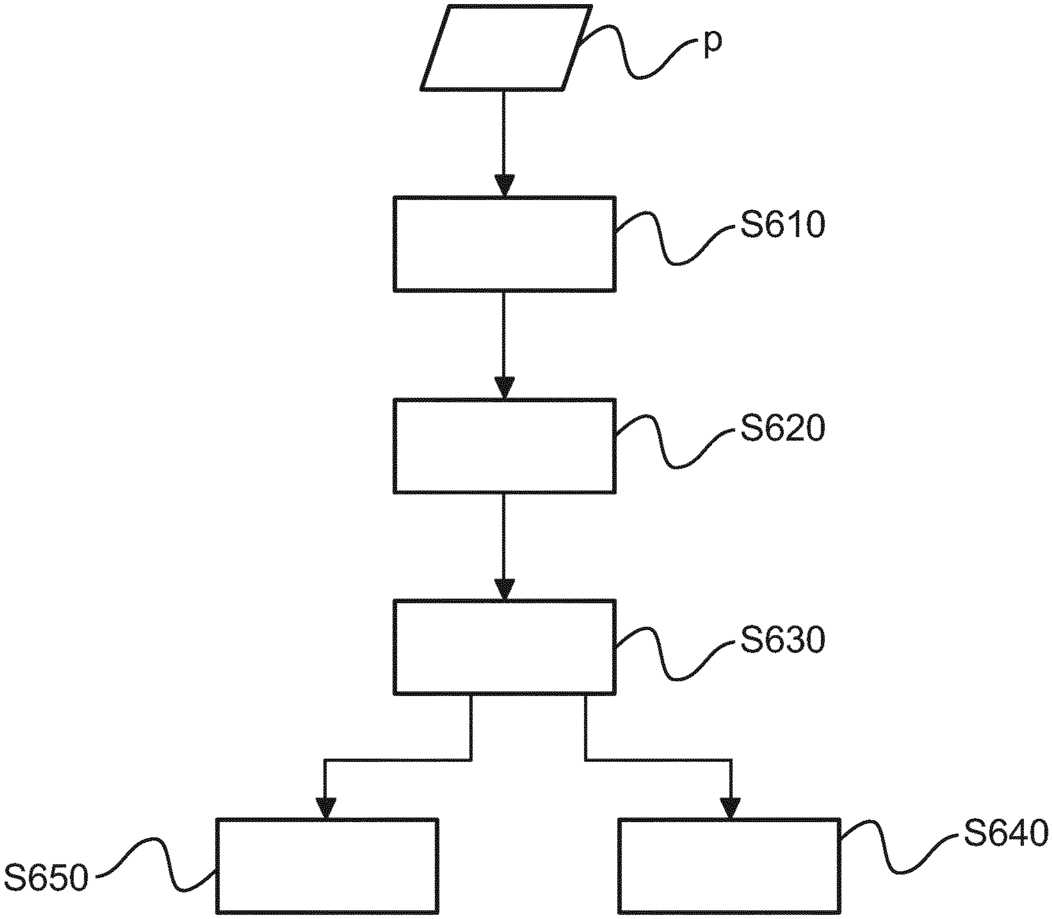
FIG. 6 shows a flow chart of a method for supporting radiation therapy.

Reference is now made to the flow chart of FIG. 6 which shows a computer implemented method of operation of the RT support SRS as described in particular relation to FIG. 2. It should be understood however that the steps described in the following are not necessarily tied to the architecture as explained above but may also be considered a teaching in their own right.

At step S610 the input image, such as one acquired with an in-room kV imaging unit, possibly associated with a radiation delivery device, is received. The input image p is preferably received before application of a fraction by a radiation delivery in radiation treatment of a given patient. In embodiments, the input image is a 2D projection image, a radiograph. The input image p can be a single frontal two dimensional (2D) image, or multiple two dimensional images acquired from several angles. For example, a frontal planar radiography can be acquired in the EBRT treatment room with the in-room kV imaging system of the RTD, such as LINAC or other. Acquiring projection images is clinical routine and are usually available anyway as a result of other workflows, such as patient positioning or other low dose non-diagnostic imagery. The radiation dose due to the acquisition of a (single) planar kV image is much smaller than the radiation dose resulting from the acquisition of a full 3D CBCT.

Alternatively still, a 2D radiograph can be reconstructed from a 3D CBCT image, or a 3D CT image volume through forward projection. This may be useful if the machine learning unit (to be used in the next step) has been trained on 2D planar imagery. In other embodiments, a 3D image, such as a CBCT, is received for analysis at step S610 and the method operates on 3D imagery rather than 2D projection images. This may be useful in particular in scenarios where 3D imagery become available anyway, such as in treatment plan verification or in other clinical workflows, not necessarily related to RT.

The input image p is then processed by a machine learning algorithm at step S620 to detect the presence of a medical condition. Exemplary conditions from the field of lung or chest imaging include, but are not limited to, any one or more of atelectasis, pleural effusion, pneumonia or inflammation.

If a medical condition is detected at step S620, at step S630 an indication for one more medical actions in relation to the detected medical condition is then provided. The indication for the one or more medical actions may be provided in graphical form, in numerical form, in text form or otherwise, preferably displayed on a display device. In addition or instead, an indication of the medial condition itself may be provided, for instance in textual, numerical or graphical form rendered on the or another display device.

The actions may include any one or more of sending a notifying message to a recipient through a communication network C or requesting a re-imaging of the patient using a different imaging modality as the one used to produce the input image p. The different medical imaging modality is in particular 3D imaging apparatus such as CT or cone beam apparatus CBCT, MRI, SPECT/PET or any other. In embodiments, the action may include starting the 3D imaging if there is an in-room 3D imaging modality in place. The requested 3D imaging, for more detailed examination of the detected medical condition, will in general incur a higher dose than the in-room kV imaging apparatus. However, the 3D imaging is used only if a medical condition is indeed detected. Daily imaging at much lower dose using the in-room kV imaging equipment can be done to ensure side effects caused by the radiation treatment, such as secondary malignancies, are caught early, quickly and with lower dose exposure compared to periodic (e.g, daily) 3D imaging. The 3D imaging is used only when required.

Another medical action may include amending the treatment plan in view of the detected medical condition. In particular, this may include suspending the ongoing treatment plan. Other treatment plan amendments may include any of changing rest periods, changing the fraction doses, and others. In addition or instead, the indicated actions may relate to other, non RT related, treatment options that should be applied to the patient. Another action may include automatically interfacing with a medical database, such as an RT logbook, and to update the patient's PAT record with the detected finding as provided by the MLU.

In general, the action may trigger application of other clinical workflows and protocols at the radiotherapy department, eg plan evaluation, but also other clinical workflows and interventions at other departments that can attend to symptoms or treat the detected lung condition. Moreover, the detected medical condition can be used to automatically fill-in/update digital logs and reports of the radiotherapy treatment. Information in relation to the detected medical condition that may be used to update/fill-in reports/logs may include any one or more of: specifics of the input image, a color coded severity classification, description of the lesion such as shift or growth, the name of the detected medical condition.

Useful and advantageous as 2D imagery, all of the above is of equal application for systems configured to detect the medial condition based on 3D imagery. This embodiment may be used for example if 3D CT imagery is available, such as in facilities equipped with in-room CT-on-rails or similar.

It will be understood, that any one or more of the above described actions are envisaged in embodiments, in any combination or sub-combination.

In an optional step S650 patient data and the detected medical condition may be correlated with a treatment outcome value. Patient data include data that describe characteristics of the patient, such as age, weight, sex, height, etc. The treatment value is indicative of a probability of a treatment outcome to be expected in relation to the patient. The treatment outcome may relate to an oncological outcome or to a side effects outcome. Oncological outcomes are related to success or failure of eradicating cancer, quantifiable statistically, such as, for example, disease free survival at 5 years after treatment, local relapse of disease after 2 years, and similar. A side effect outcome relates to any side effect that the patient might develop after receiving radiotherapy treatment, eg pneumonitis, difficulty swallowing, etc.

Figure 7:
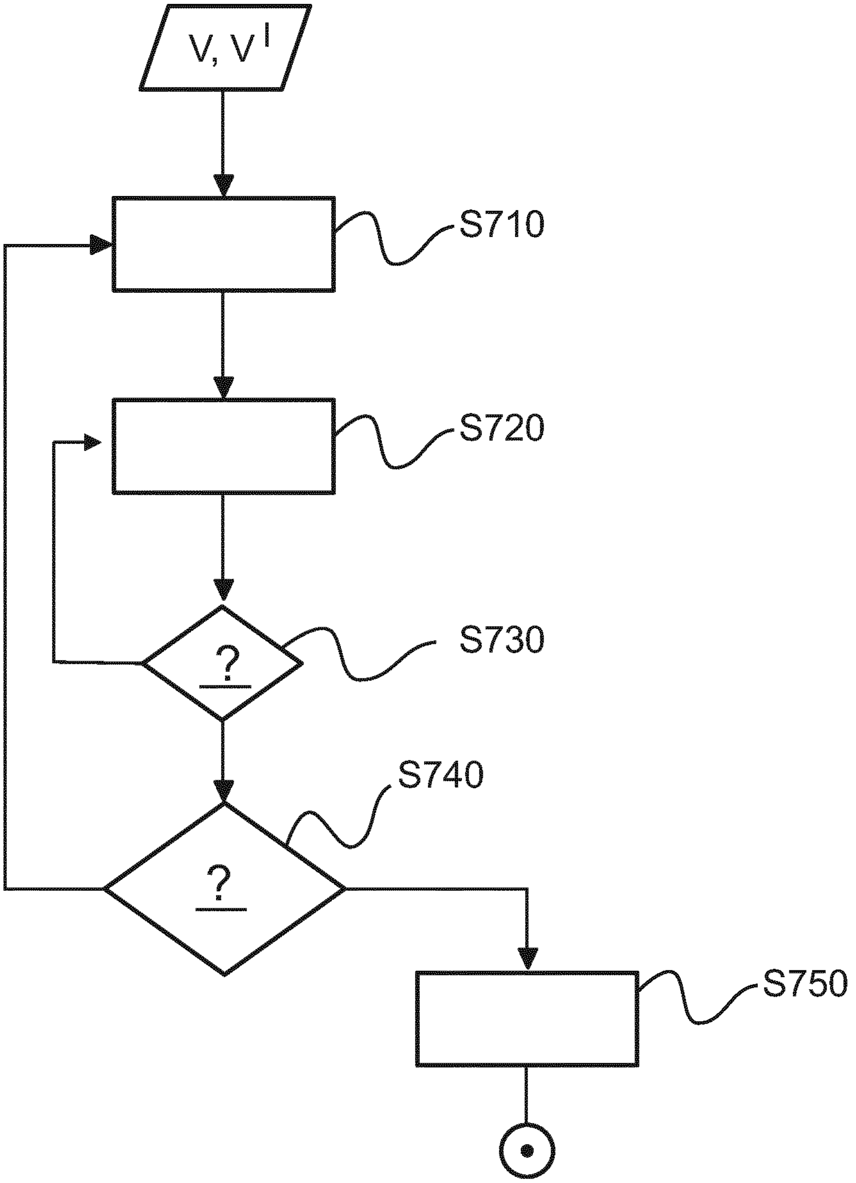
FIG. 7 shows a flow chart of a computerized method of training a machine learning model.

In optional step S640 some or all of the suggested clinical actions are initiated either automatically or by confirmation through a human user, such as clinical staff. Reference is now made to FIG. 7 which shows a flow chart of a method of training a machine learning component MLU.

At step S710 a pair of training data from corpus of training data is received. The pair includes in particular an input image v and a target v' associated with the input image v. The target encodes a particular medical condition. The input training image is in particular a historical image retrieved from records of an earlier patient. The image represents an organ of interest such as chest or lung X-ray image. The target v' is a label that indicates the medical condition that is represented in the training image v. The training input image is in particular a 2D projection image, such as an X-ray radiograph.

At step S720 the input training image v is applied to the machine learning network to produce as output a classification into a medical condition. The machine learning component has a current set of network parameters.

At step S730 the output medical condition classification M(v) is compared with the target label v' and an error is quantified, and, depending on the error, the current set of network parameters of the model Mis then adjusted. Process steps S720,S730 are then repeated until the error falls below an error threshold or until a stopping condition is fulfilled.

In particular, steps S720-730 are repeated in one or more iteration cycles until the output classification M(v) produced by the model M corresponds, within the pre-defined error threshold, to the medical condition encoded by the target v'. The correspondence between the target and the output classification is measured by a suitable similarity function $\mu(M(v),v')$.

Process flow then proceeds at step S740 to check whether there are further training data pairs available. If yes, process flow then proceeds the next training data pair in the corpus of training data and repeats the steps S710-S740 as described above.

The network parameters NP of model M are hence adapted in nested loops, with step S740 controlling the outer loop and step S S730 controlling the inner loop.

Once all or pre-set number of training data pairs have been processed the model with the, now updated, set of parameters NP is then provided at step S750 as the pre-trained machine learning model MLU ready for deployment.

The method may be used in particular for neural network architectures. Step S730 for adjusting the network parameters in the context of the inner loop may be implemented by the forward-backward propagation (FBP) algorithm, but other gradient descent schemes, such as the conjugate gradient descent methods, stochastic gradient descent methods, the BFGS (Broyden-Fletcher-Goldfarb-Shannon) method, the Nelder-Mead method, Newton-Raphson algorithms and others, or even non-gradient based optimization schemes, iterative or not, may be used instead. Other machine learning models than NN-based are also envisaged and can be trained in the framework FIG. 7.

As mentioned, in particular, and in embodiments, a convolutional neural-network CNN may be used. However, this is not at the exclusion of alternative embodiments such as support vector machines, linear regression algorithms, decision trees, or otherwise, all equally envisaged herein.

The training process may be a one-off operation or it is continued in repeated training phases to enhance performance based on newly available training data.

Preferably, if an NN or, more specifically a CNN is used, a deep architecture is envisaged with more than one hidden layers. The number of hidden layer may be in the region of two digit figures, such as in the 10s or 20s, or even higher. For feed-forward networks, as indeed envisaged herein, the number of hidden layers is the depth of the network. However, in recurrent networks the depth does not necessarily equal the number or hidden layers, but may be higher. More generally, the depth may be defined in terms of credit path length. A credit path is the number of nodes or edges traversed for given final output as produced at the output layer OL. For a recurrent network, where the credit path may traverse the whole network multiple times, the depth may be a multiple of the number of hidden layers.

All that has been said above at FIGS. 5,7 in relation to training of the MLU, is of equal application for a machine learning implementation of the correlator component CC. In this case the training data is made of pairs of patient data and associated outcome numbers.

In the above training scheme, the parameters may be initialized at random or a transfer learning scheme may be used where parameters from models, trained in other contexts than RT, may be adopted as an initial parameter set. For instance, parameters, or whole pertained models, may be used that where pre-trained on standard chest X-ray where patients are usually standing. Although in RT patients are lying, the models pre-trained on standard X-rays provide good initial models that quickly converge to models suitable for RT requirement, or such pre-trained models may in instances even work sufficiently well without further training. Transfer learning may also be used for others ROIs or anatomies and is not restricted to thoracic patients.

As mentioned, training the system to recognize the medical condition from 2D projection radiographs is preferred because of the lower dose, all of the above equally apply to 3D imagery and the system may be trained instead to operate on 3D imagery. Alternatively, a dual system may be trained, and user can then switch between 2D and 3D-image mode. In general, it is possible to train directly on 3D images. This however requires a large number of annotated 3D images. Currently, there are not too many annotated 3D CBCT images available. From a practical point of view, in a clinic, it is envisaged to start training the machine learning unit on 2D imagery, to automatically interpret the conditions in the 3D images. For this we would need to extract a 2D projection image from the 3D image, such as via forward projection.

The training system TS and/or the support system SRS may be implemented as suitable software components on a computing unit PU, either general purpose or dedicated. Preferably the decided or general purpose computing system PU may include one or more processors. In particular, one or more multi-core processors such as GPU (graphics processor unit) or TPU (tensor processing unit) may be used. A single one or a plurality of computing units may be used, possibly arranged as server(s) communicatively coupled in a communication network such as in a Cloud architecture. In particular, the computing for the machine learning component may be so outsourced to one or more servers. As an alternative to a purely software based implementation, some or all of the components of the system RCS may be implemented as hardware components such as FPGAs or ASICS.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A computerized system for radiation therapy support, comprising:

an input interface for receiving, during a therapy delivery phase, an input image comprising a 2D projection image acquired by an imaging apparatus, wherein the imaging apparatus is part of a radiation therapy delivery device, the input image representing at least a region of interest of a patient and acquired before delivery of a dose fraction, among multiple dose fractions associated with a treatment plan for the patient, by the radiation therapy delivery device;

a pre-trained machine learning unit configured for processing the input image, based on a machine learning model pre-trained on training imagery, the processing including:

applying the input image to an input layer, the input layer comprising a matrix of nodes of a neural network, wherein a node of the matrix of nodes corresponds with a pixel of the input image; and calculating an output vector, during the therapy delivery phase, the output vector including accumulated responses, wherein an index of entries of the output vector corresponds with a specified class, among a group of classes each representing a medical condition including a side effect of radiation therapy, wherein the specified class represents an indication of a presence of a respective medical condition;

a reporting component configured to provide, based on the output vector data and during the treatment delivery phase, an indication for one or more clinical actions to be performed in relation to the patient, wherein at least one of the one or more clinical actions as indicated by the reporting component includes an adaptation of the treatment plan.

2. The system of claim 1, wherein the one or more clinical actions include re-imaging the patient using a different imaging apparatus or modality.

3. The system of claim 1, wherein the reporting component comprises a communications interface, wherein the providing of the indication for the one or more clinical actions by the reporting component includes the communications interface transmitting a message through a communication network to a recipient.

4. The system of claim 1, including a visualizer configured to form an enriched image including the input image and a graphical rendering of a location in the input image in relation to the medical condition represented by the specified class.

5. The system of claim 1, wherein the machine learning unit is arranged in a neural network architecture.

6. The system of claim 1, comprising a correlator component configured to correlate patient data and the medical condition represented by the specified class with a treatment outcome value, indicative of a probability of a treatment outcome to be expected in relation to the patient.

7. The system of claim 1, comprising a knowledge builder component configured to populate, into a data repository, patient data in association with the medical condition represented by the specified class.

8. An arrangement, comprising the system of claim 1 and the radiation therapy delivery device.

9. A computer-implemented method for radiation therapy support, the method comprising:

receiving, during a therapy delivery phase, an input image comprising a 2D projection image acquired by an imaging apparatus, wherein the imaging apparatus is part of a radiation therapy delivery device, the input image representing at least a region of interest of a patient and acquired before delivery of a dose fraction, among multiple dose fractions associated with a treatment plan for the patient, by the radiation therapy delivery device;

processing, during the therapy delivery phase, to detect a medical condition including a side effect caused by radiation therapy treatment, the processing based on a machine learning model pre-trained on training imagery, the processing comprising:

applying the input image to an input layer, the input layer comprising a matrix of nodes of a neural network, wherein a node of the matrix of nodes corresponds with a pixel of the input image; and calculating an output vector, during the therapy delivery phase, the output vector including accumulated responses, wherein an index of entries of the output vector corresponds with a specified class, among a group of classes each representing a medical condition including a side effect of radiation therapy, wherein the specified class represents an indication of a presence of a respective medical condition;

providing the output vector including the indication of a presence of the respective medical condition, and providing during the therapy delivery phase, based on the output vector, an indication for one or more clinical actions to be performed in relation to the patient, wherein at least one of the one or more clinical actions includes an adaptation of the treatment plan.

10. A computer program element, which, when being executed by at least one processing unit, is adapted to cause the processing unit to perform the method of claim 9.

11. A non-transitory computer readable medium having stored thereon the program element of claim 10.

12. The method of claim 9, wherein the one or more clinical actions include re-imaging the patient using a different imaging apparatus or modality.

13. The method of claim 9, wherein the one or more clinical actions includes transmitting a message through a communication network to a recipient.

14. The method of claim 9, including forming an enriched image including the input image and graphically rendering of a location in the input image in relation to the medical condition represented by the specified class.

15. The method of claim 9, wherein the machine learning model is arranged in a neural network architecture.

16. The method of claim 9, comprising correlating patient data and the medical condition represented by the specified class with a treatment outcome value, indicative of a probability of a treatment outcome to be expected in relation to the patient.

17. The method of claim 9, comprising populating, into a data repository, patient data in association with the medical condition represented by the specified class.

18. The method of claim 9, comprising augmenting the input image, including at least one of superimposing or overlaying a class activation map (CAM) on the input image.

19. The method of claim 18, wherein the CAM identifies image pixels in the input image having contributed greater than a specified threshold to the respective medical condition represented by the specified class.

* * * * *